United States Patent
Ehrenpreis

(10) Patent No.: US 8,686,040 B2
(45) Date of Patent: Apr. 1, 2014

(54) METHOD FOR TREATING ANAL PRURITIS AND OTHER PERIANAL DISORDERS

(75) Inventor: Eli D Ehrenpreis, Skokie, IL (US)

(73) Assignee: RDD Pharma Ltd., Tel-Aviv (IL)

( * ) Notice: Subject to any disclaimer, the term of this patent is extended or adjusted under 35 U.S.C. 154(b) by 704 days.

(21) Appl. No.: 12/399,770

(22) Filed: Mar. 6, 2009

(65) Prior Publication Data

US 2009/0247635 A1 Oct. 1, 2009

Related U.S. Application Data

(60) Provisional application No. 61/041,211, filed on Mar. 31, 2008.

(51) Int. Cl.
*A61K 31/197* (2006.01)

(52) U.S. Cl.
USPC .......................................................... 514/561

(58) Field of Classification Search
USPC .......................................... 514/398, 509, 561
See application file for complete search history.

(56) References Cited

FOREIGN PATENT DOCUMENTS

| WO | WO95/06466 | * | 3/1995 |
| WO | WO00/67742 | * | 11/2000 |

* cited by examiner

*Primary Examiner* — Jennifer M Kim
(74) *Attorney, Agent, or Firm* — Burns & Levinson LLP

(57) ABSTRACT

The invention relates to methods and compositions for the treatment of pruritis ani and other perianal disorders. There are currently few treatments for these conditions, many of which have significant side effects. The methods of the invention involve the administration, in a cream or lotion of pregabalin, an anti-epileptic agent that has pain relieving properties. This topical form of pregabalin may also include the addition of other agents such as immunomodulators, antibiotics or agents that enhance wound healing. This method may be useful as a new and safe treatment for pruritis ani, skin conditions and other anorectal disorders. Previous positive clinical experience suggests that this new treatment is promising for these disorders.

2 Claims, No Drawings

METHOD FOR TREATING ANAL PRURITIS AND OTHER PERIANAL DISORDERS

CLAIM FOR PRIORITY

This Application claims priority from U.S. Provisional Patent Application Ser. No. 61/041,211 filed Mar. 31, 2008 entitled "METHOD FOR TREATING ANAL PRURITIS AND OTHER PERIANAL DISORDERS"

FIELD OF THE INVENTION

This invention is relates to a method for alleviating the major symptoms of a number of perianal disorders, including but not limited to pruritis ani (anal itching).

DETAILED DESCRIPTION

Disclosed herein is a method for delivering a substance or substances including pregabalin in a controlled manner to the anatomic area surrounding the anal opening. Anatomically, this is called the perianal area. Pregabalin, when administered orally, has been shown to possess pain-relieving properties in a number of pharmacological studies. However, it is difficult to orally provide high concentrations of Pregabalin without inducing unintended side-effects. The inventor has found that Pregabalin may be delivered directly to the perianal area using a topical delivery system, in the form of a cream, lotion or ointment. In this manner, pregabalin can be provided in high concentrations at the site of a variety of perianal diseases, with a reduced risk of side-effects.

The inventor has discovered that once applied to the perianal area, pregabalin, alone or in combination with other pharmacologically active agents would be useful in alleviating many of the symptoms of the diseases, namely, anal itching, pain, burning, edema, ulceration fistulization and bleeding. This treatment may result in complete alleviation of symptoms, total healing or remission of these conditions. It is considered that topical pregabalin provides a better means of treating these conditions than the therapeutic agents currently available for these purposes.

Diseases of the perianal area are manifested by a variety of symptoms, including anal itching, burning, pain, swelling, discharge, bleeding and tenderness. Perianal disorders can occur in childhood. Additionally, certain animals, such as cats, dogs, and horses may be affected. The prevalence of pruritis ani and other perianal diseases is currently unknown, but it is expected in total that these conditions are relatively common (affecting more than 2% of the US population). On the other hand, individual perianal diseases are rare and many of these fall under the category of orphan illnesses.

Current basic and clinical research studies suggest that pruritis ani is associated physiologic alterations of the perianal skin, the spinal cord, and the brain. Altered signaling between these systems appears to be a major factor in the enhancement and perpetuation of these conditions. Other perianal disorders, such as perianal Crohn's disease, prior radiation therapy and eczema result from altered activity of the intrinsic immune system. Local noxious stimuli in the perianal region result in negative sensory input to the brain. In this manner, the development of perianal conditions produces characteristic symptoms. Stressful or painful experiences may worsen the severity of perianal diseases as well as the perception of symptoms, known as hyperalgia.

Hemorrhoids occur when normal venous structures in the anal canal and external portion of the anus become enlarged and engorged with blood. Symptoms include anal and perianal pain, pressure, bleeding, prolapse, soiling and difficulty evacuating stool contents. Treatments include ingestion of fiber, stool softeners, oral analgesics and local anesthetics. If these treatments are unsuccessful, invasive procedures including infrared coagulation, hemorrhoidal banding and surgical hemorrhoidecomy are used. There are a several disadvantages of currently available topical therapies.

Treatment of pruritis ani and other perianal disease initially involves dietary alteration such as the elimination of caffeine containing foods, tomatoes and hot peppers. Limitation of perfumed soaps and avoidance of excessive chafing of the perianal skin may also be beneficial. Over-the counter topical creams and ointments may provide benefit as well. A study of the topical application of capsaicin has suggested that this agent may reduce symptoms. Additional drugs are used to treat perianal diseases. These have potential disadvantages. For example, local anesthetics may produce itching, skin irritation or may have limited or no efficacy. Topical corticosteroid creams and ointments such as hydrocortisone can cause atrophy or thinning of the skin, striae or stretch marks. In addition, skin bruising or tearing with minimal pressure, the development of telangiectasias or abnormal blood vessels of the skin, susceptibility to bacterial skin infections, fungal skin infections and allergic reactions to the cream or ointment vehicle may occur with topical steroid treatment. Topically applied steroids may also be absorbed from the skin and into the bloodstream. This can cause high blood pressure, elevated blood sugar, fluid retention, osteoporosis, psychiatric effects such as depression, and a large number of other side effects.

Perianal Crohn's disease is generally treated with antibiotics and immunomodulating drugs. Surgical procedures may be required for control of perianal abscesses, a common complication of perianal Crohn's disease. Topical steroids may be beneficial for perianal eczema or psoriasis. Systemic immune modulating agents may also be used for these conditions. Most local treatments for perianal disease contain local anesthetics and steroids in a topical base. The combination of local anesthetics and steroids relieve the symptoms of itching and pain as well as to reduce concomitant inflammation.

Thus, it can be surmised that limited treatment options are available for patients with pruritis ani and other perianal diseases. Many of these conditions are orphan illnesses that have received little or no attention in the pharmaceutical field. At present, pregabalin has not been proposed for the purpose of treating perianal disorders or other inflammatory skin conditions.

Pregabalin, originally released as an anti-epileptic agent, has been used for a number of additional indications. Pregabalin is a chemically structural analog of [gamma]-aminobutyric acid. Newer uses of pregabalin include treatment of neuropathic pain, including diabetic neuropathy and post-herpetic neuralgia, depression, generalized anxiety disorder, and hiccups. There are limited reports of the effectiveness of oral pregabalin for vulvodynia, tremor and ataxia as well. Thus, pregabalin may have analgesic, anticonvulsant, and anxiolytic effects. Oral pregabalin has approved for by the Food and Drug Administration for the treatment of neuropathic pain (1,2).

The physiologic mechanism for the efficacy of pregabalin in these conditions includes reduction of the influx of calcium into hyperexcited neurons. Pregabalin appears to produce this effect by binding to the [alpha]-2-[delta] subunit of voltage-gated calcium channels. These occur primarily in the brain and spinal chord. Pregabalin modulates the release of several neurotransmitters with exitory properties, including glutamate, norepinephrine, substance P, and calcitonin generelated peptide by altering these calcium currents. The result of this alteration of calcium channels is the inhibition of stimulated pain-producing neurons and their return to normal function.

Although not previously used in the past for pruritis, the mechanism of action of pregabalin may be of particular value for the treatment of itching, especially if this action is proven to take place when the drug is topically applied. Itching is felt to occur from stimulation of local C-neuron fibers that are histamine-responsive. Other theories suggest that centrally mediated suppression of the impulses from these fibers is of primary importance in reducing the symptoms of these conditions. Prior studies demonstrating the efficacy of capsaicin applied directly to the perianal skin in patients with pruritis ani confirm the concept that topical agents may work in this condition. Unfortunately, capsaicin will initially cause burning and marked discomfort when initially applied.

[Gamma]-amino butyric acid analogs, including pregabalin, have been studied extensively in the laboratory and in clinical medicine. When administered by mouth, these drugs have been shown to have pain relieving properties. Most studies have pointed to the role of the central nervous system as the site of these effects. Pregabalin, a pro-compound of gabapentin, has improved pharmacokinetic properties, including higher lipid solubility than gabapentin. Pregablin has greater than 90% absorption when administered orally and reaches a peak concentration within 90 minutes after oral ingestion. On the other hand, gabapentin has a 60% bioavailability, which diminishes with increasing doses. These improved pharmacokinetic properties suggest that pregabalin has promise as a topically applied agent.

To investigate the possibility of using topical pregabalin for the treatment of a perianal disorders, a 10% pregabalin cream was administered to a 75 year old patient with greater than 30 years of severe and incapacitating pruritis ani. This symptom was refractory to a large number of over-the-counter and prescription remedies for the condition, including topical local analgesics and steroids. This patient described an 80% improvement in symptoms and quality of life following eight weeks of twice/day therapy. A second patient with intermittent anal pruritis had complete symptomatic relief following one to two applications of 10% pregabalin cream at the time when flaring of symptoms developed. A third patient with severe perianal Crohn's disease had mild improvement of perianal discomfort with a few intermittent topical applications of 10% pregabalin cream. A fourth patient with eczema of the elbows had almost complete resolution of symptoms with topical pregabalin. Accordingly, the present embodiment presents methods for topical application of pregabalin as a novel and improved treatment for symptomatic perianal diseases including pruritis ani, perianal Crohn's disease, anal eczema, hemorrhoids, anal fissure and other perianal conditions associated with pain and/or inflammation.

A first embodiment of the invention consists of a topical form of pregabalin in concentrations from 1 to 50% by weight with a topical delivery vehicle.

A variety of substances may be utilized to create the vehicle in which the pregabalin in mixed. These may include substances that enhance the efficacy of the product by increasing efficacy by direct action on the perianum including the perianal skin. These substances may include moisterizers, emollients, preservatives, topical antimicrobials, oils, fats, fatty acids, petroleums, lubricating agents, vitamins, gums and herbal enhancing agents (See list II).

The aforementioned embodiment may optionally include other topical medication for enhancing the efficacy of treatment for perianal disease, including one or more of the following (List I):

1) calcium channel blockers;
2) Alcoholic extracts of yeast have been used as the active ingredient in medications under names such as "tissue or skin respiratory factor," Biodyne (Sperti Drug Co, Cincinnati, Ohio—now defunct), and live yeast cell derivative (LYCD);
3) Local anesthetics;
4) Nitroglycerin;
5) Rutaecarpine, an alkaloid isolated from *Evodia rutaecarpa;*
6) Corticosteroids;
7) Tacralimus, an immunosuppressant that has been used as a topical treatment for perianal Crohn's disease;
8) Metronidazole, an antibiotic used for the treatment of Crohn's disease;
9) Thalidomide, an anti-inflammatory agent used for the treatment of Crohn's disease;
10) Dapsone, an antibiotic and anti-inflammatory agent used for the treatment of Crohn's disease;
11) Cyclosporine, an immunosuppressant that has been used as a topical treatment for perianal Crohn's disease;
12) Ciprofloxacin, an antibiotic used for the treatment of Crohn's disease;
13) Peppermint oil, a natural local anesthetic;
14) Capscacin, a naturally occurring local anesthetic;
15) Vitamins such as beta caroteine, retinyl palmitate, vitamin A and vitamin E that enhance wound healing; and
16) Pentosan polysulfate sodium, enhancing wound healing.

In order to produce a topical form of pregabalin, alone or in combination with the aforementioned substances, a vehicle for topical application will be required. The following is a list of potential ingredients that will make up the vehicles for producing the cream or ointment containing pregabalin. The use of additional vehicles are not limited by this list (List II).

| LIST II | |
|---|---|
| Lanolin | 8-hydroxyquinoline sulfate |
| petroleum | Water |
| isostearic acid | stearic acid |
| steareth-21 | sodium lactate |
| PPG 12/SMDI copolymer | Polypethylene glycol |
| Aceylates/C10-30 Alkyl Acrylate Crosspolymer | Alanine |
| Alcohol denatatured | Allantoin |
| *Aloe* | Alpha-Dodecyl-omega-hydroxypoly(oxyethylen)-2 |
| Aluminum Starch Octensylsuccinate | Aluminum Stearate |
| water | Arginine |
| ascorbic acid | vitamin A |
| vitamin E | fish oil |

-continued

| LIST II | |
|---|---|
| medium chain triglycerides | Oatmeal |
| Benzoic Acid | BHT |
| Biosaccharide Gum-1 | Biotin |
| Bisabolol | Butyl Methoxydibenzoylmethane |
| *Butyrospermum parkii* (Sheabutter) | *Buxus chinensis* (Jojoba Oil) |
| C12-15 Alkyl Benzoate | Caprylic/Capric Triglyceride |
| Carbomer | Cera alba |
| Cera microcristallina (microwax) | Ceresin (microwax) |
| Ceteareth-6 | 12 and 20 |
| Cetearyl Alcohol | Cetearyl Isononanoate |
| Cetearyl Octanoate | Cetyl Alcohol |
| Cetyl Dimethicone | Cetyl Dimethicone Copolyol |
| Cetyl Palmitate | *Chamomilla recutita* |
| Citric Acid | Cocamide DEA |
| Cocamide MEA | Cocamidopropyl Betaine |
| Coco Caprylat/Caprate | Coco Glucoside |
| Coconut Acid | Cyclomethicone |
| Decyl Oleate | Dicaprylyl Ether |
| Dimethicone | Dipentaerythrityl Hexacaprylate/Hexacaprate |
| Dipropylene Glycol | Disodium ETDA |
| Disodium Laureth Sulphosuccinate | Disodium Lauroamphodiacetate |
| Disodium Lauryl Sulphosuccinate | Ethoxydiglycol |
| Ethylhexyloxyglycerin | Glycerin |
| Glycerol Monostearate | Glyceryl Caprate |
| Glyceryl Caprylate | Glyceryl Lanolate |
| Glyceryl Oleate and stearate | Glycine |
| *Glycine soja* (soja oil) | *Hamamelis virginiana* |
| *Helianthus annuus* | Castor Oil |
| corn oil | coco butter |
| Isoeicosane | Isohexadecane |
| Isopropyl Myristate | Isopropyl Palmitate and Stearate |
| sodium polyacrylate | Lauryl Glucoside |
| Lecithin | *macadamia* oil |
| Magnesium Stearate and sulfate | Methoxy PEG-22/Dodecyl Glycol Copolymer |
| Methylparaben | MIPA-Laureth Sulphate |
| Myristyl Alcohol | Myristyl Myristate |
| Octyl Cocoate | Octyl Dodecanol |
| Octyl Stearate | *Oenothera biennis* (evening primose oil) |
| Ozokerite (microwax) | Panthenol |
| Paraffin | Paraffinum liquidum (liquid paraffin) |
| PEG-Dicocoate | Pentaerythrityl Tetraisostearate |
| *Persea gratissima* (Avocado oil) | Phenoxyethanol |
| Phenyl Trimethicone | Poloxamer 101 |
| Poloxamer 124 | Polyaminopropyl Biguanide |
| Polydecene | Polyglyceryl-2 Caprate |
| Polyglyceryl-2 Dipolyhydroxystearate | Polyglyceryl-3 Diisostearate |
| Polyglyceryl-3 Methylglucose Distearate | Polyquaternium-10 |
| Potassium Phosphate | Potassium Sorbate |
| PPG-15 Stearyl Ether | PVP/Hexadecene Copolymer |
| Propyl Gallate | Propylene Glycol Octanoate Decanoate |
| Propylene Glycol | Propylparaben |
| *Prunus dulcis* (almond oil) | *Ribes nigrum* (black cu Sodium Carbomer |
| Sodium Cetearyl Sulphate | Sodium Chloride |
| currant oil) | *Ricinus communis* (castor oil) |
| Salicylic acid | white willow bark |
| bromelain | Serine |
| Sodium Benzoate | Sodium Bicarbonate |
| Sodium C14-16 Olefin Sulfonate | Sodium Citrate |
| Sodium Cocoamphoacetate | Sodium Cocoyl Isethionate |
| Sodium Corn Starch Octenylsuccinate | Sodium Hyaluronate |
| Sodium Hydroxymethyl Glycinate | Sodium Isostearoyl Lactylate |
| Sodium Lactate | Sodium Laureth Sulphate |
| Sodium Lauryl Sulphoacetate | Sodium Myreth Sulphate |
| Sodium PCA | Sodium Phenylbenzimidazole Squalane |
| Sulfonate | Sodium Salicylate |
| Sorbitan Isostearate | Sorbitan Stearate |
| Sorbitol | Steareth-2 |
| Steareth-20 | Steareth-21 |
| Stearic Acid | Stearyl Alcohol |
| Synthetic and natural Beeswax | Tocopheryl Acetate |
| Tridecyl Stearate | Tridecyl Trimellitate |
| Triisostearin | Trisodium EDTA |
| *Triticum vulgare* (wheat oil) | Ubiquinone (coenzyme Q10) |
| Urea | Xanthan Gum |
| *Zea mays* | Zinc Oxide |
| Zinc Sulphate | Lidocaine |

-continued

LIST II

| | |
|---|---|
| tetracaine | Benzocaine |
| prilocaine | green tea extracts |
| copper peptides | coenzyme Q10 |
| kinetin | Alpha |
| beta and polyp hydroxyl acids | palm oil |
| plant emulsifier | Allantoin |
| babassu oil | Behentrimonium Methosulfate (and) Cetearyl Alcohol |
| *Calendula* Petals (*Calendula officinalis* | Coffee Butter (*Coffea arabica* Seed Oil (and) Hydrogenated Vegetable Oil) |
| Diazolidinyl Urea (and) Iodopropynyl Butylcarbamate | Emulsifying Wax NF |
| Flaxseed (Linseed) Oil (*Linum Usitatissimum* | Honey |
| Kaolin Clay (China Clay) | Kokum Butter |
| Magnesium Sulfate | Marshmallow Root Powder (*Althea officinalis* |
| Meadowfoam Seed oil (*Limnanthes Alba* Seed oil | Modified Wheat Star Olive oil (*Olea europaea* |
| c *Gardenia Taitensis* | MSM (Methylsulfonylmethane |
| Palm Kernel oil (*Elaeis guinnesis* Kernel Oil | Panthenol |
| Phenoxyethanol (and) Caprylyl Glycol (and) Sorbic Acid | Polysorbate 20 (Vegetable Emulsifier |
| Rhassoul Clay (also called Ghassoul | Rice Bran Oil (*Oryza Sativa* |
| Rosehip Powder (*Rosa canina*) | Virgin Oil de Coco-Creme (*Cocos nucifera*) |
| live yeast cell derivative (Bio-Dyne) | shark oil |
| Eucerin | |

According to one embodiment the inactive carrier is Eucerin which is a commercially available create whose ingredients include: Aqua, Polyglyceryl-3 Methylglucose Distearate, Cyclomethicone, Glycerin, Cetearyl Alcohol, Lactic Acid, Sorbitan Stearate, Panthenol, PEG-150 Distearate, Serine, Gly-cine, Lecithin, Alanine, Bisabolol, Xanthan Gum, Titanium Dioxide, Trisodium NTA, Disodium Phosphate, Potassium Phosphate, Diazolidinyl Urea, Butylparaben, Isobutylparaben, Propylparaben, Ethylparaben, Methylparaben, Phenoxyethanol, Parfum.

A first embodiment of the invention is a method for treating anorectal disorders, the method comprising the steps of providing a composition including an active ingredient including between 1% and 50% pregabalin and a non-active carrier used to deliver the active ingredient, and topically applying the composition to the anatomic area surrounding the anal opening. Additionally, this product may be useful for the treatment of pruritis and diseases of other portions of the skin including the skin of the head, appendages and the rest of the body. The carrier may be in the form of a cream, ointment or lotion. This invention will be used to deliver the pregabalin with or without additional ingredients directly to the sites of action in the anorectal region, thereby avoiding dilution of the properties of these substances that occurs with oral ingestion.

The composition of the invention may be formulated as a 1% up to 50% pregabalin by weight in a cream, ointment or lotion. The optimal concentration of pregabalin are determined by the results of preliminary studies and can vary with the age, size, and weight of the subject (patient). The components of these creams and lotions will be determined by effectiveness of mixing with pregabalin, stability of compounds produced, ease of use of theses lotions and creams, enhancement of efficacy of the mixtures and patient tolerance and efficacy of creams and lotions produced. The invention also contemplates mixing pregabalin 1% to 50% concentration by weight in a matrix containing the aforementioned ingredients. The final product will consist of a cream, ointment or lotion.

Additionally, the invention encompasses a composition combining pregabalin with a variety of other agents (as listed above) that enhance the efficacy of pregabalin for treating pruritis ani and other perianal conditions. The invention includes the placement of pregabalin in a variety of vehicles for enhancement of mixing of pregabalin as well as to improve the treatment of the perianal conditions. These substances will include moisterizers, emollients, preservatives, topical antimicrobials, oils, fats, fatty acids, petroleums, lubricating agents, vitamins, gums and herbal enhancing agents.

Some of the components of these creams, ointments or lotions of pregabalin will include pharmaceutically acceptable carriers including any and all solvents, dispersion media, coatings, antibacterial and antifungal agents, isotonic, and absorption-delaying agents and the like. The use of such media and agents for pharmaceutically-active substances is well known in the art. Except insofar as any conventional media or agent is compatible with the active ingredient, its use in the therapeutic compositions is contemplated.

Supplementary active ingredients may be incorporated into the compositions. These include but are not limited to anti-inflammatory agents, immunomodulating agents, antibiotics, vitamins such as beta caroteine, retinyl palmitate, vitamin A and vitamin E, and agents that enhance wound healing.

The compositions and/or methods disclosed and claimed herein can be made and executed without undue experimentation, in light of the present disclosure. While the compositions and methods of this invention have been described in terms of preferred embodiments, it will be apparent to those of skill in the art that variations may be applied to the compositions and/or methods and in the steps or in the sequence of the steps of the method described herein, without departing from the concept, spirit, and scope of the invention. More specifically, it will be apparent that certain agents which are both chemically and physiologically related may be substituted for the agents described herein, while the same or similar results would be achieved. All such similar substitutes and modifications apparent to those skilled in the art are deemed to be within the spirit, scope, and concept of the invention, as defined by the appended claims.

The references cited herein throughout to the extent that they provide exemplary procedural or other details supplementary to those set forth herein, are all incorporated herein by reference.

What is claimed:

1. A method for treating pruritis ani in a subject in need thereof, the method comprising the steps of: providing a composition comprising pregabalin as an active ingredient in an amount between 1% and 50% and a non-active carrier used to deliver the active ingredient; and topically applying the composition to the anatomic area surrounding an anal opening.

2. The method of claim 1 wherein the composition further comprises at least one of calcium channel blockers, thalidomide, alcoholic extracts of yeast, live yeast, live yeast cell derivative (LYCD), dapsone, local anesthetics, cyclosporine, nitroglycerin, ciprofloxacin, rutaecarpine, peppermint oil, corticosteroids, capscacin, tacralimus, metronidazole, and pentosan polysulfate sodium.

\* \* \* \* \*